United States Patent [19]

Lines et al.

[11] 4,009,122

[45] Feb. 22, 1977

[54] NOVEL GLYCOL SOLUBLE MOLYBDENUM CATALYSTS AND METHOD OF PREPARATION

[75] Inventors: Ellwood L. Lines, Westville; John A. Herbst, Madison; Robert J. Fairbrother, Wallingford, all of Conn.

[73] Assignee: Olin Corporation, New Haven, Conn.

[22] Filed: June 23, 1975

[21] Appl. No.: 589,346

[52] U.S. Cl. .................... 252/431 N; 260/348.5 L; 260/429 R
[51] Int. Cl.$^2$ .......................................... B01J 31/02
[58] Field of Search ............ 252/431 N; 260/429 R, 260/348.5 L

[56] References Cited

UNITED STATES PATENTS

| | | | |
|---|---|---|---|
| 3,285,942 | 11/1966 | Price et al. | 260/429 R |
| 3,668,227 | 6/1972 | Mattucci et al. | 260/348.5 L X |

Primary Examiner—Patrick P. Garvin
Attorney, Agent, or Firm—F. A. Iskander; T. P. O'Day

[57] ABSTRACT

Novel glycol soluble molybdenum catalysts and a method of preparing them are described. The catalysts, which are useful in epoxidation reactions, are prepared by reacting an oxygen-containing molybdenum compound, an amine, and an alkylene glycol, at elevated temperatures.

22 Claims, No Drawings

NOVEL GLYCOL SOLUBLE MOLYBDENUM CATALYSTS AND METHOD OF PREPARATION

The present invention is directed to novel compositions and to the method of making these compositions. More particularly, the present invention is directed to novel molybdenum catalysts which are prepared by reacting an oxygen-containing molybdenum compound with an amine and an alkylene glycol.

Various alkylene oxides have been produced by a variety of methods including the well-known chlorohydrin techniques, the direct oxidation techniques using $O_2$ and a catalyst, and the indirect oxidation techniques such as those employing peroxidic compounds and a catalyst. Among those in which an alkylene compound is oxidized with a peroxidic compound by catalysis to obtain the alkylene oxide, the methods in which the compounds of molybdenum are used as catalysts appear to be very promising. Thus, for example, U.S. Pat. No. 3,778,451 to Michel Poite describes the preparation of propylene oxide by reacting hydrogen peroxide with propylene in the presence of propylene glycol molybdate and a nitrogenous base, and U.S. Pat. No. 3,489,775 to Irenee Seree de Roch et al describes a similar epoxidation using as a catalyst the reaction product of molybdenum compounds, such as molybdic acid, and organic nitrogenous bases. The present invention is directed to molybdenum-type catalysts and the method of preparing them, but catalysts of the present invention are different from those heretofore described. It should be noted that apparently the only prior art which describes the reaction product of molybdenum oxides, glycols and nitrogenous compounds somewhat similar to the present invention is U.S. Pat. No. 3,285,942 to J. A. Price et al, but this patent describes reacting these components in proportions different from those used in the present invention and results in the preparation of oxidation inhibitors rather than oxidation promotors such as in the present invention. Thus, the unique catalysts of the present invention are reaction products resulting from the reaction of specified amounts of an oxygen-containing molybdenum compound, an amine and an alkylene glycol, and are useful epoxidation catalysts. They are particularly advantageous due to their high solubility in the epoxidation reaction medium, their easy synthesis, reproducibility and handling, and their mitigation of epoxidation reaction mixture contamination.

The molybdenum catalysts of the present invention, as mentioned, are reaction products resulting from the reaction of an oxygen-containing molybdenum compound, an amine, and an alkylene glycol. The oxygen-containing molybdenum compound may be, for example, the ammonium salt of molybdic acid, or it may be one containing only oxygen and molybdenum atoms, e.g., molybdenum dioxide, molybdenum sesquixode, molybdenum trioxide or mixtures of these. The preferred molybdenum starting material is molybdenum trioxide.

The amine starting material employed in the preparation of the novel catalysts of the present invention is a compound having the formula $R_1R_2R_3N$ wherein $R_1$, $R_2$, and $R_3$ are each independently selected from hydrogen, substituted and unsubstituted alkyls having about 1 to about 10 carbon atoms, preferably about 1 to about 6 carbon atoms, and substituted and unsubstituted aryls having about 6 to about 10 carbon atoms, preferably about 6 to 8 carbon atoms, with the proviso that at least one of $R_1$, $R_2$, and $R_3$ is not hydrogen. Thus, primary, secondary and tertiary amines may be used, although the tertiary amines are preferred. Additionally, the amine starting materials used to produce the molybdenum catalysts of the present invention include the N-oxides of the tertiary amine compounds of the above formula. Preferred among the amine starting materials are tertiary amines wherein $R_1$, $R_2$, and $R_3$ are each independently methyl, ethyl or butyl, and the N-oxides of these.

The alkylene glycol starting material may be any alkylene glycol having about 2 to about 10 carbon atoms and will preferably have about 2 to about 4 carbon atoms, for example, ethylene glycol, propylene glycol, butylene glycol, and the like. Among the most preferred are ethylene glycol and propylene glycol and mixtures of these.

The essential starting materials of the present invention may be combined with a solvent and reacted or may be reacted without a solvent. Generally an organic solvent is used, if desired, which is compatible with and inert to all of the reactants involved. The alcohols, and preferably the secondary alcohols, e.g., isopropanol and sec-butanol, are especially suited for this purpose. No criticality is found in the amount of solvent used, if any. But as a practical commercial consideration about 0 to about 300 or more moles, for example, about 1 to about 30 moles, of solvent per mole of molybdenum reacted may be employed.

In the method of making the molybdenum catalysts of the present invention, the oxygen-containing molybdenum compound, the amine, and the glycol are combined, with or without solvent, and reacted at elevated temperatures. Generally, about 0.1 to about 4 moles of amine and preferably about 0.5 to about 2 moles of amine are used per mole of molybdenum. About 1.5 moles to about 20 moles of the glycol, and preferably about 1.8 to about 3 moles of the glycol are employed per mole of molybdenum. The reactants are combined with the oxygen-containing molybdenum compound in any order and heated to an elevated temperature. For example, a temperature of about 70° C. to about 160° C. and preferably a temperature of about 80° C. to about 150° C. may be used depending upon the particular reactants and solvent employed.

The oxygen-containing molybdenum compound, the amine, and the glycol react to produce a molybdenum catalyst and the reaction may be run for about 15 minutes or even less to about 12 hours or more depending upon the reactants and the reaction temperature chosen, but generally the reaction is completed to a satisfactory degree in about 0.3 hours to about 3 hours.

Upon completion or substantial completion of the reaction of the essential starting materials used in the present invention, the catalyst produced is generally in liquid form. In those instances where the catalyst formed included a solvent, the catalyst may be separated from the solvent by any known method, e.g., stripping or it may be used in solution without solvent removal. Whether the catalyst is prepared with or without solvent, the entire reaction product may be effectively used as a catalyst and no separation is necessary or any excess amine may be removed, e.g., by stripping, if desired. Further, whether or not a solvent is employed, the reaction product may be, for example, filtered to obtain useful catalyst supernatant liquid.

The novel catalysts obtained by the method of the present invention are believed to be molybdenum compounds having molybdenum-oxygen central bonding with glycol capping and with amine or ammonium groups possibly attached to molybdenum by ionic or coordination bonds or both. However, the novel catalysts of the present invention are the reaction products of the above-mentioned starting materials. The concept that they are molybdenum compounds having glycol capping with amine or ammonium groups is theoretical speculation, and the novel catalysts should not be construed to be limited thereto.

As mentioned, the molybdenum catalysts of the present invention are useful in the preparation of various organic epoxides produced by indirect oxidation in which a peroxidic compound is employed as the oxygen contributor. Alkylene compounds characterized by an olefinic unsaturation i.e., having the functional group $>C=C<$, are oxidized to obtain the corresponding alkylene oxide. The term alkylene is used herein to include both substituted and unsubstituted compounds and encompasses any organic compound having an olefinic bond which may be oxidized with hydrogen peroxide in the presence of a metal compound catalyst. Among the alkylenes which may be oxidized by the catalysts of the present invention are ethylenic hydrocarbons having, for example, 2 to 10 carbon atoms. e.g., 3 to 6 carbon atoms. For example, ethylene, propylene, butene, hexene, etc. as well as polyethylenic hydrocarbons, such as butadiene or isoprene, and cyclic compounds such as cyclohexene or styrene may be epoxidized. Additionally, substituted compounds such as ethylenic alcohols, e.g., allyl alcohol, ethylenic halides, e.g., allyl chloride, as well as unsaturated oils and fats may be oxidized with the catalysts of the present invention.

The alkylene is preferably oxidized in the liquid phase although gaseous alkylene may be employed, e.g., by bubbling the alkylene gas through a catalyst solution. When desired, elevated pressures may be used so as to maintain the alkylene material in the liquid phase. Generally, an appropriate solvent is used which is compatible with and inert to both the alkylene and the peroxidic compound. An organic solvent of a polar nature sufficient to obtain a homogeneous mixture with the alkylene and the hydrogen peroxide is preferred. The alcohols, especially the secondary alcohols, e.g., isopropanol and sec-butanol, as well as glycols, esters, e.g., isopropyl acetate, linear or cyclic ethers and a few weak carboxylic acids are preferred.

Typically, for the epoxidation reaction, the organic solvent may contain the peroxidic compound, e.g., hydrogen peroxide, in solution, and this solution may be combined with the alkylene to produce a reaction solution. When this technique is employed, about 1 percent to about 50 percent or more, preferably about 5 percent to about 30 percent of peroxidic compound is used based on the weight of the solvent. Also, in order to retard the co-production of undesirable organic compounds such as glycols, it is preferred to have no more than a minor amount of water present during oxidation. Because the oxidation of the alkylene may produce, and when $H_2O_2$ is used, does produce water by-product, the peroxidic compound feed preferably contains less than 10 percent water, for example, less than 1 percent water, based on the weight of the epoxidation reaction feed.

The alkylene is generally reacted with the peroxidic compound, e.g., hydrogen peroxide, in at least an equivalent amount based on the number of olefinic groups per molecule of alkylene to be oxidized. When the alkylene has only one olefinic bond, then at least an equimolar amount of it is used with the peroxidic compound, e.g., about 1 to about 5 moles, preferably about 1 to about 2 moles, of alkylene per mole of peroxidic compound is used. As mentioned, the oxidation of the alkylene is preferably carried out in the liquid phase and in a single solvent solution.

The peroxidic compound may be any commercially available product or it may be crude, e.g., produced on site by known methods. For example, solutions of hydrogen peroxide in isopropanol are obtained by oxidation of isopropanol with oxygen at elevated temperatures. In this case, the produced solution, after undesirable byproducts such as acetone are at least partially removed, may be employed in the alkylene oxidation and the isopropanol will become the solvent for the alkylene oxidation reaction solution.

The molybdenum catalysts of the present invention are used to promote the alkylene oxidation and are soluble in reaction solutions such as those described above. Generally, the catalyst should be used in an effective amount to obtain commercially acceptable yields. An effective amount will vary depending upon the specific catalyst used, the particular alkylene compound or compounds being epoxidized and the reactor design and its flow through characteristics such as residence time. In general, about 0.01 to about 0.60 or so gram-atoms of molybdenum per liter of reaction solution and preferably about 0.04 to about 0.30 gram-atoms are used. In other words it is desirable to have about 0.004 to about 0.15 moles of molybdenum per mole of alkylene compound, and preferably about 0.008 to about 0.075 moles, in the reaction solution, although more catalyst may be used without detrimentally affecting epoxidation.

The alkylene oxidation reaction employing a molybdenum catalyst of the present invention may be performed in a batch operation or it may be a continuous process. In either case the reaction will generally be completed to a commercially acceptable degree within a short period of time, and actual residence time will, as suggested, depend upon the particular reactor design and operating conditions employed. The alkylene oxidation reaction is generally carried out in the range of about 0° to about 80° C., and preferably about 20° to about 60° C., at a pressure, for example, sufficient to maintain the oxidation reaction solution in the liquid phase. The oxidation of the alkylene may be satisfactorily completed within a matter of minutes, or it may take days but is generally completed within about 5 hours, e.g., 2 or 3 hours, more or less.

During the oxidation reaction, the peroxidic compound gives up an oxygen atom to the alkylene to effect epoxidation. A product mixture may contain water, and will contain water when the peroxidic compound is $H_2O_2$. The product mixture will also contain the alkylene oxide, the molybdenum catalyst and undesirable organic by-products. Because the water which may be formed enhances the production of undesirable glycols, it is desirable to maintain the amount of water in the reaction mixture at a minimum. When a batch system is employed, the production of undesirable glycol may be mitigated by maintaining the total amount of water present at the end of the reaction below about 20 percent by weight based on the total weight of the reaction mixture. When a continuous system is used, water may be removed from the reaction mixture by removal of a portion of the reactants, separation of the water by evaporation techniques and recycle of the non-aqueous constituents, or alternatively the reaction mixture may have a sufficient amount of solvent so as to produce a low water content product mixture on a continuous basis.

The reaction product containing the desired alkylene oxide obtained by use of a catalyst of the present invention may be subjected to distillation or other separation technique and the usable constituents, e.g., unreacted alkylene, solvent, etc. and the molybdenum catalyst may be recovered and recycled to the system desired. Also, the degree of purification of the alkylene oxide employed depends upon the ultimate utility of the alkylene oxide and is a matter of choice.

The following examples illustrate various embodiments of preparing and using the novel molybdenum catalysts of the present invention without limiting the scope of the present invention thereto:

EXAMPLE 1

To a suitable reactor with a $H_2O$ cooled condenser to prevent removal of volatiles overhead, is charged 1875 g of $MoO_3$ (13.03 mol), 1981 g of propylene glycol (26.06 mol) and 879.1 g of triethylamine (8.69 mol). The reactants are stirred and heated, reflux occurs at about 90° C., but quickly disappears (bp $NEt_3$ 89° C.) and then the reactants are heated to about 130° C. This temperature is maintained for about 0.5 hours. The reaction mixture is then cooled and filtered. No $NEt_3$ odor is detected after reaction completion.

Filtration of material prepared in this manner reveals at most the presence of about 0.6% solids, indicating a solubilization of molybdenum greater than 99%. These solids are determined to contain Mo,C,H,N,O. The greater than 99% conversion is a minimum assuming the solid precipitate is all $MoO_2$ and the presence of the C, H and N suggests an even higher conversion based on the total molybdenum present.

The molybdenum catalyst solution is analyzed by NMR and thermal gravimetric analysis (TGA). The TGA analysis yields a weight loss of about 46% by 250° C. and a total weight loss at 700° C. of about 60.5%. These values agree well with the theoretical loss of propylene glycol (41.9%) and the loss of propylene glycol and $NEt_3$ (60.3%).

Elemental analysis is:

| | Elemental analysis is: | | | |
|---|---|---|---|---|
| | Theory (%) | Ratio | Experimental (%) | Ratio |
| Mo | 26.40 | 1.50 | 26.66 | 1.53 |
| C | 33.03 | 14.99 | 33.10 | 15.10 |
| H | 7.16 | 38.70 | 7.10 | 38.50 |
| N | 2.57 | 1 | 2.54 | 1 |
| Kjehldahl N | 2.57 | 1 | 2.59 | 1 |

In relation to characterization of catalyst obtained, it is estimated that about 20 to 30% of the propylene glycol of the catalyst is coordinated to the molybdenum, with free and coordinated propylene glycol undergoing facile exchange. The exact manner of linkage between the propylene glycol and the molybdenum is not known. The $NEt_3$ is known to be present as $+HNEt_3$ and coordination bonding to the molybdenum is suspected.

The highest ratio of coordinated PG to Mo is Mo/PG = 1/60; (3.33/2) the lowest 1/.40 (5/2) (dissolved in 1.6 to 1.4 mols PG). These are analytical limits. The compound could be described as follows:

$(MoO_3) . (0.40 - 0.60$ "PG"$) . (0.66 +HNEt_3)$ That is:

3 $MoO_3$ . 1.2 – 1.8 PG . 2 +$HNEt_3$ dissolved in 4.8 to 4.2 mols PG.

Stability tests show that samples standing for more than 400 days exhibit little or no precipitation or instability.

EXAMPLE 2

In this Example, triethylamine N-oxide is substituted for trialkylamine. A reactor is charged with 5.00 g (.03475 mol) $MoO_3$, 12.78 g $Et_3NO . H_2O$ (0.07645 mol $Et_3NO$, i.e., about 70% triethylamine N-oxide) 5.28 g (0.06497 mol) propylene glycol and 15 ml of isopropanol. This suspension is stirred and warmed to reflux (about 83° C.). After about 15 min. at reflux temperature, all the $MoO_3$ is dissolved into the yellow solution which is obtained. The solution is then stripped of isopropanol on a rotary evaporator leaving a brown oil. Conversion of $MoO_3$ into a soluble form of Mo is determined to be about 100%. This product is an effective epoxidation catalyst if used within a short time after preparation. A strong amine odor is evident after about fifteen days of standing, suggesting deterioration at that time.

EXAMPLE 3

A reactor having a heater, reflux condenser and an agitator is charged with 20 g (0.139 moles) of molybdenum trioxide, 112.5 g (1.480 moles) of propylene glycol and 64.5 g (0.499 moles) dibutylamine. The mixture is stirred and heated to 130°–160° C. Agitation is maintained in the temperature range for about 2 hours and then cooled to room temperature. The cooled amber brown colored reaction mixture is filtered or used "as is" for an epoxidation catalyst. Conversion (solubilization Mo): 100%.

EXAMPLE 4

A reactor of the type used in the above Examples is charged with 70.59 g molybdic acid (ammonium salt) (0.417 mol Mo), 63.39 g of propylene glycol (0.834 mol) and 28.13 g $NEt_3$ (0.278 mol). This mixture is stirred and heated at reflux temperature for about seven hours to produce a brownish solution. The suspension is filtered, and cooled, yielding approximately 5 g of a tan solid. The % Mo analysis on the solid indicates that about 94% of the Mo in the molybdic acid is converted by the reaction into a soluble form, the brown oil filtrate. The Mo/N ratio in the brown oil is determined to be about 1.5/1 and the brown oil is found to be a useful epoxidation catalyst.

EXAMPLE 5

A reactor of the type mentioned is charged with 40.00 g $MoO_3$ (0.2780 mol), 28.12 g $NEt_3$ (0.2780 mol), 34.47 g of ethylene glycol (0.556 mol) and 50 ml of isopropanol. The suspension is stirred and heated to reflux and is maintained at reflux for about 1.5 hours to produce a greenish solution. After cooling to room temperature, isopropanol and excess $NEt_3$ (0.09174 mol) is stripped on a rotary evaporator. The greenish solution is then filtered to remove trace solids; % Mo analysis on the solution indicates a solubilization conversion of Mo of about 97%. The final Mo/N ratio in the solution is 3.2/1. Some precipitation occurs upon storage, but the product is found to be an effective epoxidation catalyst.

EXAMPLE 6

A stainless steel pressure vessel is charged with 110 grams of 20% (± 2%) solution of total peroxidic compound in isopropanol (a total of 0.582 moles of $H_2O_2$, remainder organic peroxides) and 7.5 grams of the novel molybdenum catalyst prepared by the method of Example 1 (corresponding to 0.021 moles of molybdenum). The pressure vessel is immersed in a 30° C. batch, and 42 grams (1 mole) of liquified propylene is then charged to the sealed pressure vessel at a pressure of about 140 psi. The epoxidation reaction mixture is stirred and maintained at 30° C. for about 4 hours.

Samples of the product mixture are analyzed and found to contain about 10 grams of propylene oxide.

EXAMPLE 7

Example 6 is repeated except that an equimolar amount of butylene is substituted for the propylene, and the reaction is carried out at atmospheric rather than at an elevated pressure. The product mixture is found to contain butylene oxide.

EXAMPLE 8

Example 6 is repeated except that the catalyst of Example 4 is used in place of the Example 1 catalyst. The reaction product mixture is found to contain a substantial amount of propylene oxide.

What is claimed is:

1. A method of preparing a molybdenum catalyst comprising:
reacting at elevated temperatures between about 70° and about 160° C an oxygen-containing molybdenum compound selected from the group consisting of molybdenum dioxide, molybdenum sesquioxide, molybdenum trioxide, the ammonium salt of molybdic acid, and mixtures of these, with about 1.5 to about 20 moles of an alkylene glycol per mole of molybdenum and about 0.1 to about 4 moles of an amine per mole of molybdenum, the amine being selected from the group consisting of:
a. a compound of the formula $R_1R_2R_3N$ wherein $R_1$, $R_2$ and $R_3$ are each independently selected from the group consisting of hydrogen, unsubstituted alkyls having about 1 to about 10 carbon atoms, and unsubstituted aryls having about 5 to about 10 carbon atoms, with the proviso that at least one of $R_1$, $R_2$, and $R_3$ is not hydrogen, and
b. an N-oxide of a tertiary amine compound of the above formula.

2. The method of claim 1 wherein the alkylene glycol has 2 to 10 carbon atoms.

3. The method of claim 2 wherein about 1.8 to about 3 moles of an alkylene glycol are included as a reactant.

4. The method of claim 1 wherein the oxygen-containing molybdenum compound is selected from the group consisting of molybdenum dioxide, molybdenum sesquioxide, molybdenum trioxide and mixtures of these.

5. The method of claim 4 wherein the $R_1$, $R_2$, and $R_3$ of the amine are each independently selected from the group consisting of unsubstituted alkyls having about 1 to about 6 carbon atoms.

6. The method of claim 5 wherein about 1.8 to about 3 moles of alkylene glycol and about 0.5 to about 2 moles of the amine are reacted per mole of molybdenum.

7. The method of claim 6 wherein the alkylene glycol has 2 to 4 carbon atoms.

8. The method of claim 7 wherein the alkylene glycol is propylene glycol.

9. The method of claim 6 wherein the amine is a tertiary amine, or its N-oxide, in which $R_1$, $R_2$, and $R_3$ are each independently selected from the group consisting of methyl, ethyl and butyl.

10. The method of claim 9 wherein the amine is triethylamine.

11. The method of claim 10 wherein the oxygen-containing molybdenum compound is molybdenum trioxide.

12. The reaction product prepared by the method of claim 1.

13. The reaction product prepared by the method of claim 2.

14. The reaction product prepared by the method of claim 3.

15. The reaction product prepared by the method of claim 4.

16. The reaction product prepared by the method of claim 5.

17. The reaction product prepared by the method of claim 6.

18. The reaction product prepared by the method of claim 7.

19. The reaction product prepared by the method of claim 8.

20. The reaction product prepared by the method of claim 9.

21. The reaction product prepared by the method of claim 10.

22. The reaction product prepared by the method of claim 13.

* * * * *